(12) United States Patent
Räsänen et al.

(10) Patent No.: US 9,469,581 B2
(45) Date of Patent: Oct. 18, 2016

(54) CATALYTIC REFINING OF TERPENES OF PULP ORIGIN

(75) Inventors: Jari Räsänen, Imatra (FI); Tapani Penttinen, Huutjärvi (FI); Ali Harlin, Espoo (FI); Reetta Kaila, Espoo (FI)

(73) Assignee: Stora Enso OYJ, Helsinki (FI)

( * ) Notice: Subject to any disclaimer, the term of this patent is extended or adjusted under 35 U.S.C. 154(b) by 111 days.

(21) Appl. No.: 13/701,658

(22) PCT Filed: Jun. 3, 2011

(86) PCT No.: PCT/FI2011/050518
§ 371 (c)(1),
(2), (4) Date: Mar. 12, 2013

(87) PCT Pub. No.: WO2011/151526
PCT Pub. Date: Dec. 8, 2011

(65) Prior Publication Data
US 2013/0165721 A1    Jun. 27, 2013

(30) Foreign Application Priority Data
Jun. 3, 2010  (FI) .................................. 20105630

(51) Int. Cl.
*C10G 1/00* (2006.01)
*C07C 5/22* (2006.01)
(Continued)

(52) U.S. Cl.
CPC ............... *C07C 5/41* (2013.01); *C07C 5/2775* (2013.01); *C09F 3/00* (2013.01); *C07C 2529/08* (2013.01); *C07C 2529/18* (2013.01); *C07C 2529/70* (2013.01)

(58) Field of Classification Search
CPC ......... C10G 1/00; C07C 5/22; C07C 5/2206; C07C 5/373; C07C 15/00; C07C 15/02
USPC ................................ 585/240, 242, 408, 432
See application file for complete search history.

(56) References Cited

U.S. PATENT DOCUMENTS

| 3,130,007 A | 4/1964 | Breck |
| 3,778,485 A | 12/1973 | Prochazka |

(Continued)

FOREIGN PATENT DOCUMENTS

| EP | 0 243 238 | 10/1987 |
| EP | 0 267 833 | 5/1988 |

(Continued)

OTHER PUBLICATIONS

Roberge et al., Catalytic aspects in the transformation of pinenes to p-cymene, Applied Catalysis A: General 215 (1-2), pp. 111-124, 2001.*

(Continued)

*Primary Examiner* — In Suk Bullock
*Assistant Examiner* — Philip Louie
(74) *Attorney, Agent, or Firm* — Patterson Thuente Pedersen, P.A.

(57) ABSTRACT

Biobased p-cymene and methods of producing same, which can further be converted to terephtalate. Further, a method is described for converting crude sulfate turpentine recovered from chemical wood pulping into p-cymene and eventually to terephtalic acid of biological origin, and products thereof respectively. In said method, both conversion and desulfurization is realized in one reaction step. The disclosure is also related to use of zeolite catalysts in said method.

11 Claims, 6 Drawing Sheets

(51) Int. Cl.
    *C07C 5/13*         (2006.01)
    *C07C 5/41*         (2006.01)
    *C07C 5/27*         (2006.01)
    *C09F 3/00*         (2006.01)

(56) References Cited

U.S. PATENT DOCUMENTS

| | | |
|---|---|---|
| 3,778,486 A | 12/1973 | Hamby, Jr |
| 4,382,152 A | 5/1983 | Wideman |
| 4,665,252 A | 5/1987 | Hoelderich et al. |

FOREIGN PATENT DOCUMENTS

| | | |
|---|---|---|
| FR | 2 243 246 | 4/1975 |
| RU | 2 200 144 C1 | 3/2003 |
| SU | 332115 | 4/1972 |
| SU | 929676 | 5/1982 |

OTHER PUBLICATIONS

Bazhenov et al., Hydrogenation and Skeleton Rearrangement of a-Pinene on Heterogeneous Catalysts, Russian Journal of Applied Chemistry 76 (2), pp. 234-237, 2003.*
Haber et al., Manual of Method and Procedures for Catalyst Characterization, International Union of Pure and Applied Chemistry, vol. 67, Nos. 8/9, pp. 1257-1306, 1995.*
Monteiro, J. L. F., Veloso, C. O., Catalytic conversion of terpenes into fine chemicals, *Top. Catal.* 27 1-4 (2004) 169-180.
Wang (Huaxue Shijie (2001), 42(3), 131-133 CODEN: HUAKAB; ISSN: 0367-6358.
Hörderlich, Applied Catalysis, A: General (2001), 215(1-2),111-124 CODEN: ACAGE4; ISSN: 0926-860X.
Bazhenov et al. in Russian Journal of Applied Chemistry (Translation of Zhurnal Prikladnoi Khimii) (2003), 76(2), 234-237 CODEN: RJACEO; ISSN: 1070-4272.
Otto and Herbst, in Zellstoff and Papier (Leipzig) (1980), 29(2), 59-61 CODEN: ZLPAAL; ISSN: 0044-3867.
Casbas et al. (Applied Catalysis (1989), 50(1), 87-97 CODEN: APCADI; ISSN: 0166-9834.
Casbas et al. (Studies in Surface Science and Catalysis (1991), 59 (Heterog. Catal. Fine Chem. 2), 201-8 CODEN: SSCTDM; ISSN: 0167-2991.
Al-Wadaani, F., Kozhevnikova, E. F., Kozhevnikov, I. V., Zn(II)—Cr(III) mixed oxides as efficient bifunctional catalyst for dehydroisomerization of α-pinene to *p*-cymene, (*Appl. Catal., A.-Gen.* 363 (2009) 153-156.
Research Report VTT-R-02732-1010 (10); Roberge, D. M., Buhl, D., Niederer, J. P. M., Hölderich, W. F., Catalytic aspects in the transformation of pinenes to *p*-cymene, *Appl. CataL, A-Gen.* 215 (2001) 111-124.
Babu, G. P., Murthy, R. S., Vapour phase isomerization and aromatization of C10 cyclic olefins on supported platinum catalysts, *Res. Ind.* 34 (1989) 273-276.).
Sen, S.E. et al. (1999) Organic transformations using zeolites and zeotype materials. Tetrahedron 55 (44), pp. 12657-12698; abstract; p. 12658, fourth paragraph, line 4; Table 1, Zeolites X/Y.
Kumakiri, I. et al. (1999) Preparation of zeolite A and faujasite membranes from a clear solution. Industrial and Engineering Chemistry Research 38 (12), pp. 4682-4688; abstract; p. 4682, left column, first paragraph, lines 11 and 12; Table 1: FAU X and FAU Y).
Schuster, C. et al. (2000) Modification of faujasites to generate novel hosts for 'ship-in-a-bottle' complexes. Catalysis Today 60 (3), pp. 193-207; abstract; The title in combination with the first sentence in the abstract; section 2.2.1; Table 1: NaX.

\* cited by examiner

US 9,469,581 B2

CATALYTIC REFINING OF TERPENES OF PULP ORIGIN

PRIORITY CLAIM

This application is a National Phase entry of PCT Application No. PCT/FI2011/050518, filed Jun. 3, 2011, which claims priority from Finland Application No. 20105630 filed Jun. 3, 2010, the disclosures of which are hereby incorporated by referenced herein in their entirety.

FIELD OF THE INVENTION

The present invention is related to biobased p-cymene, which can further be converted to terephtalate. More specifically, it discloses a method for converting sulfate turpentine present in chemical wood pulping into p-cymene and eventually to terephtalic acid of biological origin. It is also related to use of zeolite catalysts in said method.

BACKGROUND OF THE INVENTION

The need for biobased reagents, chemicals and products replacing oil-based, traditional raw materials is constantly growing. Applications for this bioreplacement are entering new fields.

Terephtalic acid is the main monomer of the dominant polyester polymers, finding wide use in textiles, technical applications, packaging especially bottles and films. One of these polymers, polyethylene terephtalate (PET) is a thermoplastic polymer resin of the polyester family and is used in synthetic fibres. It has several benefits like high transparency, low weight, very good mechanical characteristics, good barrier properties, good form stability, high recyclability, health authorities' approval (e.g. FDA, EU) and economic production.

For bioreplacement in polyethylene terephtalate (PET) and polybutylene terephtalate (PBT) it is essential to find efficient production routes for the terephtalic acid. Paracymene (p-cymene) is a common precursor for oxidative production of terephtalic acid of plant-based limonene, terpinenes, and pinenes, which are recoverable in citrus fruit peals, tee three oil, turpentine respectively, and through isoprenoid pathway of carbohydrates. When applying commercial oxidation process for the cymene, yield of 90% of terephtalic acid is achieved.

It is desirable to increase the value of crude sulfur turpentine (CST) by converting it to a more valuable chemical, such as p-cymene. p-Cymene is an aromatic hydrocarbon that can be utilized as raw material in the synthesis of polymers, but there are also many other applications for p-cymene e.g. in the production of fine chemicals (Monteiro, J. L. F., Veloso, C. O., Catalytic conversion of terpenes into fine chemicals, *Top. Catal.* 27 1-4 (2004) 169-180). Industrially, p-cymene is produced by alkylation of toluene with propene.

Worldwide production of pinenes was 0.33 Mton/year based on FAO statistics on 1995. Of this 70% was sulfate turpentine CST from wood in chemical pulping processes, consisting 90% alpha- and beta-pinenes. However, the pulping process originated aromates contain sulfur, which causes problems in further refinement of pinenes, especially poisoning the catalyst and leaving an unacceptable odor to PET eventually produced from terphtalate.

Some processes for the conversion of pinenes into cymenes are known. Determination of liquid phase reaction conditions and selection of catalyst for preparation of p-cymene from α-pinene has been reviewed by Wang (Huaxue Shijie (2001), 42(3), 131-133 CODEN: HUAKAB; ISSN: 0367-6358). The preparation of p-cymene from α-pinene was studied by ring-opening-isomerization and hydrogen transfer disproportionation with a catalyst like Raney nickel, copper formate, and p-toluenesulfonic acid.

Pinenes can be dehydrogenated and aromatized in presence of Pd-catalyst close to atmospheric pressure and 200-400° C. temperature, based on Hörderlich, Applied Catalysis, A: General (2001), 215(1-2),111-124 CODEN: ACAGE4; ISSN: 0926-860X. The dehydrogenation of α-pinene to p-cymene is conducted over carriers impregnated with Pd. An optimal acid strength is required to cleave selectively the C—C bond in the cyclobutane ring of α-pinene. Too strong acid sites such as in zeolites favor side reactions like oligomerization and cracking Too weak acid sites fail to cleave the aforementioned C—C bond and rapid hydrogenation of the α-pinene is a consequence. Hydrogenolysis is also a major side reaction leading to tetramethylcyclohexanes. A reaction mechanism is proposed in which first isomerization is involved followed by hydrogenation/dehydrogenation to stabilize the components. The catalyst has a dual-functionality with the acid sites in charge of isomerization and the metallic sites responsible of hydrogenation/dehydrogenation. The use of crude sulfate turpentine (CST) as raw material shows that β-pinene has a similar reactivity as α-pinene and high yields of p-cymene can be obtained from this cheap starting material. The sulfur remains however a major drawback. The process yields 65% from pinenes and 59% of the turpentines. However, when applying CST, sulfur must be removed, because it poisons the catalyst rapidly.

Bazhenov et al. in Russian Journal of Applied Chemistry (Translation of Zhurnal Prikladnoi Khimii) (2003), 76(2), 234-237 CODEN: RJACEO; ISSN: 1070-4272, reported hydrogenation and isomerization of α-pinene on zeolite Y and heterogeneous nickel catalysts. Nickel catalyst supported on alumina reached 80% conversion in 2 hours at 400-450° C. and 0.5 MPa hydrogen pressure. However, nickel is especially sensitive for sulfur.

Kutuzov et al. disclose in RU 2200144, a process for skeletal isomerization and dehydrogenation of α-pinene in presence of zeolite-containing cracking catalyst (Z-10) preliminarily activated for 1-2 hours at 300-550° C. in nitrogen flow. Process is carried out for 2-8 hours at 150-170° C. and 5 atmospheric nitrogen pressure. The reaction is typically robust for sulfur and yields 80% conversion to p-cymene.

However, even when not harmful for the process, the remaining sulfur may be undesirable in the end products, i.e. in plastics intended for food packages. As such, it requires separate processes for sulfur removal. Removal of sulfur-containing compounds from sulfate wood turpentine has been studied widely.

Chudinov et al. disclose in SU 332115 removal of sulfur impurities from turpentine oil by treatment with sodium hypochlorite solution in the presence of a mineral acid.

Another document, U.S. Pat. No. 3,778,485 discloses purification of crude sulfate turpentine by agitating with sodium hypochlorite solution containing 90 g/l available Cl followed by washing. The composition of the bleached turpentine was α-pinene 76.4, camphene 1.3, β-pinene 13.8, myrcene 2.2, dipentene 3.6, pine oil 2, heavies 0.6, S (weight/volume) 0.014, and chloride (weight/volume) 0.092.

In U.S. Pat. No. 3,778,486, the turpentine hydrocarbon fraction was desulfurized by a multistage activated carbon (C) sorption process. Thus, the turpentine fraction containing 500 ppm of sulfur (S) was first stripped of light ends boiling below α-pinene, contacted with C, and the S-laden C regenerated in a plurality of steps. The first step was done at 150° C. and continued until the S content in the stripped phase was not substantially >50 ppm S. The second step was done at 250-300° C. and was continued for a time sufficient to remove all S in C.

Further, according to FR 2 243 246 the turpentine hydrocarbon fraction was purified by adsorption with activated C in several stages, each permitting desulfurization.

Otto and Herbst, in Zellstoff and Papier (Leipzig) (1980), 29(2), 59-61 CODEN: ZLPAAL; ISSN: 0044-3867, stated that in the desulfurization of crude turpentine by air-stripping, the amount of $Me_2S$ as S compound present in highest concentration in turpentine decreased with increasing stripping time, temperature, and amount of air used. It was calculated that treatment of turpentine containing 710 mg/l $Me_2S$ with air of 30 l/h for 83 min produces turpentine oil containing 240 mg/l $Me_2S$.

Matyunina et al. proposed in SU 929676, that variety of sorbents which can be used is expanded by treating sulfate turpentine with a carbonaceous residue resulting from the combustion of ground vegetable fuel having an adsorption activity of 45-50% with respect to iodine and 120-150 g/dm³ bulk density with subsequent regeneration of a sorbent.

Patent EP 243238 discloses a desulfurization catalyst for terpenes obtained in papermaking targeting desulfurizing without significant changes in composition by treatment with H in the vapor phase over Co—Mo oxide catalysts on active charcoal. A terpenic fraction containing α-pinene and 88 ppm S was hydrogenated at 200°/1 atm, space velocity 0.2/h, and H-terpene mol ratio 7:1 over a catalyst containing 7% CoO and 4.4% $MoO_3$ on active charcoal, resulting in 88.6% desulfurization and a 7.3% conversion of terpene; vs. 72 and 54, respectively, when a carene fraction was treated over a CoO—$MoO_3$ catalyst.

Further EP 267833 discloses a catalysts comprising CoO and $MoO_3$ on an inorganic support containing a basic alkali or/and a basic alkaline earth compound. Said catalyst is applicable to the desulfurization of terpenic oils (byproduct from manufacture of paper) by treatment in the vapor phase with H. A catalyst (catalyst A) containing 7 w-% CoO and 4.4 w-% $MoO_3$ was prepared by impregnating silica beads (sp. surface: 250 m-/g; porous volume: 0.6 mL/g) with a solution of Co nitrate and ammonium heptamolybdate, and subsequently drying and calcination at 500° C. for 6 hours. A second catalyst (catalyst B) containing CoO 7, $MoO_3$ 4.4, and $Na_2O$ 2.5% was prepared similarly except that molybdenum was first introduced in the form of $Na_2MoO_4$ and then Co was introduced in the form of its nitrate and that after drying and calcination at 500° C. for 6 hours, the catalyst was impregnated with aqueous NaOH. β-Pinene was treated with catalyst A at 200° and catalyst B at 295° and a $H_2$:terpene ratio of 7. Catalyst A eliminated 95% of the S but with a transformation rate of 85.4% for β-pinene whereas catalyst B showed 95% elimination of S and a β-terpene transformation rate of only 12%. 3-Carene and α-pinene were desulfurized similarly.

Catalytic hydrodesulfurization of terpenes was studied by Casbas et al. (Applied Catalysis (1989), 50(1), 87-97 CODEN: APCADI; ISSN: 0166-9834). Na-doped Co—Mo catalysts were used at 200-280° C. and 1 atm to desulfurize terpene fractions containing α- and β-pinene and Δ3-carene. The best results were obtained with special procedures for Na addition. The surface acidity and isomerizing activity of the catalysts were controlled throughout their preparation by $NH_3$ thermodesorption and certain probe reactions. The presence of thiophenic compounds and, to a lesser extent, the competitive adsorption of terpenes and S-containing molecules could limit the desulfurization.

Further, Casbas et al. (Studies in Surface Science and Catalysis (1991), 59 (Heterog. Catal. Fine Chem. 2), 201-8 CODEN: SSCTDM; ISSN: 0167-2991) have introduced a process and a catalyst for the sulphur removal from turpentine fractions by hydrodesulfurization (HDS) avoiding isomerization and cracking of the terpenes. β-Pinene, one of the most fragile terpenes, was used as a reference throughout the study. Carbons present, alone, a significant HDS activity, but the degradation of β-pinene varies from less than 1% for the most inert support to about 100% for the most active one. On these carbon supports, dipentene is the main product of transformation of β-pinene. Impregnation of cobalt and molybdenum between two layers of sodium ions (sodium molybdate, cobalt nitrate and finally sodium hydroxide) give the best results in HDS of β-pinene: less than 10% degradation and 80% desulfurization.

SUMMARY OF THE INVENTION

Considering the state of the art discussed above, the problem to be solved is to find a simpler process for obtaining p-cymene, which is capable of using sulphurous starting materials without a separate step for desulfurization. Such a process should involve a catalyst, which is not sensitive to contamination by sulfur or derivatives thereof, while it is capable of effectively converting pinenes into cymenes.

More specifically, there is a need to find an alternative method for conversion of sulfur contaminated pinene, in particular α-pinene, into p-cymene at a single step by use of a suitable catalyst, without the step of desulfurization. The starting material could be CST obtained as a side flow from KRAFT-pulping. The catalyst should not be sensitive to contamination by sulfur or derivatives thereof, and it should catalyze both isomerization and dehydrogenation reactions involved. The biobased p-cymene obtained should be free from sulfur contamination and useful for being turned to biobased terephtalate or terephtalic acid, forming a raw material for production of 100% biobased PET.

The solution according to embodiments of the invention is a method for the production of p-cymene, wherein the starting material comprises at least one pinene in gas phase, and the catalyst for conversion of the pinene to p-cymene comprises zeolite, the zeolite having a molar ratio $SiO_2/Al_2O_3$ of at least 3.

A feature of the invention lies in the uncomplicated nature of the method, which involves simultaneous desulfurization and conversion of terpenes to produce p-cymene. An effective catalyst not sensitive to contamination by sulfur or derivatives thereof is hereby provided.

The inventors of the present invention have surprisingly found that p-cymene can be produced from high sulfur-content pinene-source with satisfactory yield using the zeolite-based catalyst as defined above. In one embodiment, said method can be realized as a one-step process wherein desulfurization and conversion from terpenes into cymene proceed in one reactor. As a result, biobased p-cymene is obtained with high yield calculated from the α-pinene contained in the starting material terpene. According to an embodiment, desulfurized p-cymene is obtained in a single step process from sulfurous starting material such as CST.

The starting material for the conversion may have a sulfur content of at least 0.15 w-%. In one particular embodiment, the sulfur content is in the range of 0.2-1.0 w-%, covering CSTs from standard sulfate pulping processes.

In one aspect of the invention, there is provided a method for producing p-cymene, wherein the starting material comprises at least one pinene in gas phase, and the above-mentioned zeolite catalyst for the conversion. The conversion comprises consecutive isomerization and dehydrogenation reactions. In one particular embodiment, the pinene comprises α-pinene. According to an embodiment, the starting material comprising α-pinene comprises CST, which can be originated from KRAFT pulping.

In one particular embodiment, the zeolite catalyst has a molar ratio $SiO_2/Al_2O_3$ in the range of 5.2 to 7.5, still more particularly in the range of 5.5 to 6.

In a particular embodiment, said catalyst comprises Y-faujasite zeolite. The catalyst is applied in the temperature range of 177-400° C., and particularly the temperature range is from 300 to 350° C. According to an embodiment, the catalyst is pretreated at temperature of 300-500° C. under vacuum.

In one particular embodiment, the zeolite catalyst used in the invention is free from impregnated or doped transition metal or noble metal compounds, which have been included in the catalysts described in the prior art.

According to an embodiment, the reaction is performed under $N_2$ or burnt air, which may be realized under $N_2$ pressure of 1-30 bar and/or $N_2$ flush. Flushed $N_2$ effectively sweeps away the hydrogen, which liberated from the pinene starting material, preventing it from forming by-products that would reduce the desired p-cymene yield.

In another embodiment of the invention, there is provided p-cymene, wherein the carbon skeleton is of biobased origin obtainable from wood material. Particularly, said p-cymene is obtained by the method of the invention, most particularly by refining a sideflow of pulping.

In yet another embodiment of the invention, conversion product of a pinene is provided, said product comprising at least 60 w-% of p-cymene, 0.1-20 w-% of menthene, 0.1-20 w-% of menthane, 0.1-0.3 w-% of isomers of pinenes, and the remainder of impurities.

Furthermore, embodiments of the invention cover a method for producing p-cymene, wherein the starting material comprises at least one pinene in gas phase, and a catalyst for conversion of said pinene to p-cymene substantially consists of zeolite, being free from added transition or noble metal compounds. Particularly, the zeolite has a molar ratio $SiO_2/Al_2O_3$ of at least 3, and more particularly, the zeolite consists of Y faujasite zeolite. The specific embodiments as described above and defined in subclaims 2-3 and 5-13 respectively apply to this particular method, too.

In a further embodiment of the invention, there is provided use of Y faujasite catalyst for conversion reaction of α-pinene to p-cymene. According to an embodiment, sulfur or derivative(s) thereof is/are present in the conversion reaction. In one particular embodiment, the raw material comprising α-pinene is CST.

DETAILED DESCRIPTION OF THE INVENTION

Starting Material

Terpenes are a large and varied class of hydrocarbons, produced primarily by a wide variety of plants, particularly conifers, though also by some insects such as termites or swallowtail butterflies, which emit terpenes from their osmeterium.

They are the major components of resin, and of turpentine produced from resin. The name "terpene" is derived from the word "turpentine". In addition to their roles as end-products in many organisms, terpenes are major biosynthetic building blocks within nearly every living creature.

Figure 1:
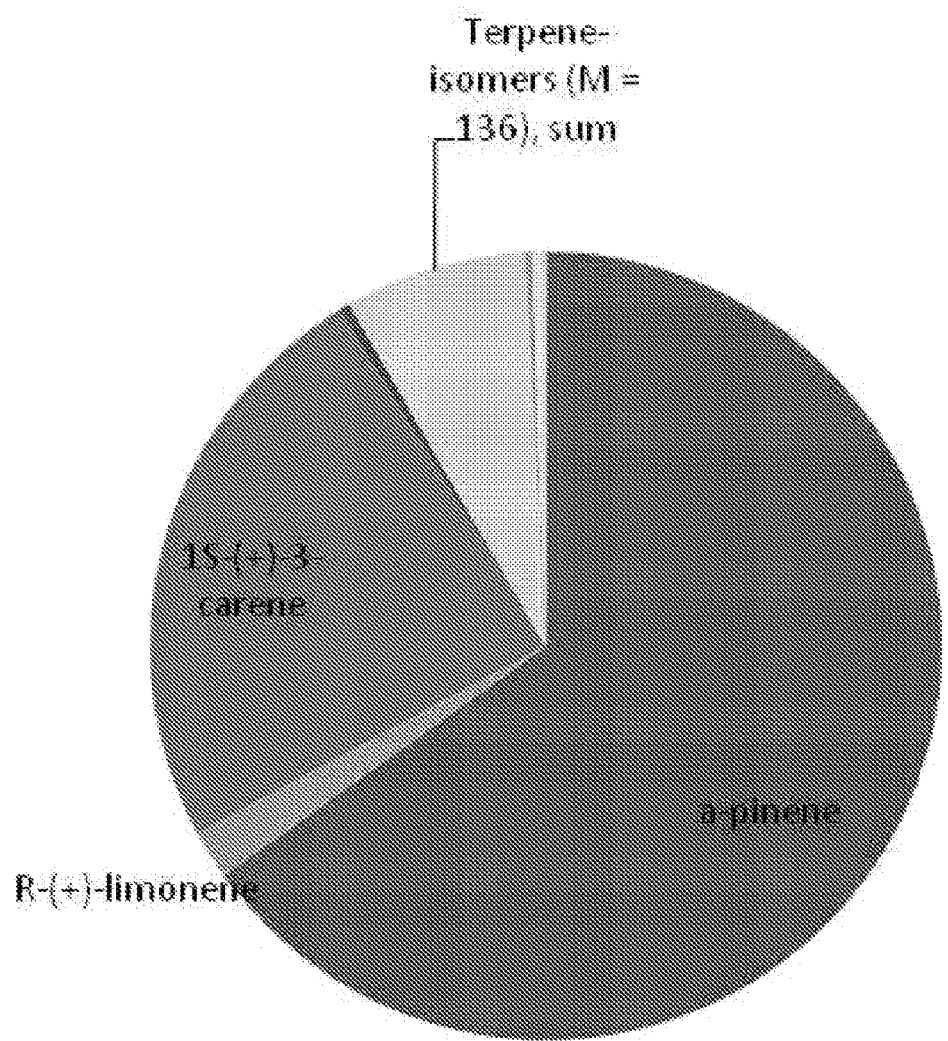
FIG. 1. provides a schematic diagram of the composition of crude sulfur turpentine (CST) from pulp and paper industry in Finland.

Turpentine (also called spirit of turpentine, oil of turpentine, wood turpentine, gum turpentine, white spirit) is a fluid obtained by the distillation of resin obtained from trees, mainly pine trees. It is composed of terpenes, mainly the monoterpenes α-pinene and β-pinene. It is sometimes known colloquially as turps, but this more often refers to turpentine substitute (or mineral turpentine). Within this specification, "crude sulfur turpentine" (CST) refers to sideflow from pulp and paper industry, comprising mainly α-pinene (roughly two thirds), a percent or two of limonene, approximately a quarter of 3-carene and the rest of terpene isomers, illustrated also in FIG. 1. Naturally the composition is dependent on the processes and raw material applied, yet this is the most common composition from KRAFT-pulping in Finland as an example. Due to use of sulfur derivatives in pulping, the ability to tolerate and remove sulfur is essential for the processes and catalysts when CST as raw material is used. Contrary to expectations based on literature, using crude sulfur turpentine comprising α-pinene as starting material for the conversion to p-cymene proved to have unexpected benefits discussed below.

The chemical compound pinene is a bicyclic terpene ($C_{10}H_{16}$, 136.24 g/mol) known as a monoterpene. There are two structural isomers found in nature: α-pinene and β-pinene.

As used herein, "at least one sulfur derivative" refers to sulfur or any derivative, inorganic or organic thereof. The sulfur and derivatives thereof present in CST are typically residues from the raw material and/or the pulping process. They may have undergone reactions during recovery and separation from other waste streams. Typical compounds comprise $CH_3SH$, $(CH_3)_2S$ and the like. It is understood that depending on the origin and preceding treatment of the raw material containing α-pinene, the sulfur derivatives may vary. However, in general, it is important to prevent or inhibit sulfur derivatives contaminating or deteriorating the end products, such as PET.

In one particular embodiment, the method according to the present invention the pinene comprises α-pinene.

Conversion from a-pinene to p-cymene

The reaction path from α-pinene to p-cymene goes via two consecutive reactions. The first reaction step is isomerization of α-pinene to its isomers (M=136 g/mol) such as limonene, menthadiene, terpinolene, and terpinenes. The isomerization is fast and takes usually place on acidic sites of the catalyst, but in the absence of catalyst also at elevated temperatures (>200° C.). The intermediates react on the catalyst surface further by dehydrogenation (or aromatization) to p-cymene (M=134 g/mol). For the latter step metallic sites, such as Zn—Cr, Pd or Pt, on the catalysts are proposed in literature (Al-Wadaani, F., Kozhevnikova, E. F., Kozhevnikov, I. V., Zn(II)-Cr(III) mixed oxides as efficient bifunctional catalyst for dehydroisomerization of α-pinene to p-cymene, (Appl. Catal., A.-Gen. 363 (2009) 153-156. RESEARCH REPORT VTT-R-02732-1010 (10); Roberge, D. M., Buhl, D., Niederer, J. P. M., Hölderich, W. F., Catalytic aspects in the transformation of pinenes to p-cymene, Appl. Catal., A-Gen. 215 (2001) 111-124; Babu, G. P., Murthy, R. S., Vapour phase isomerization and aromatization of C10 cyclic olefins on supported platinum catalysts, Res. Ind. 34 (1989) 273-276.). CST contains, however, sulfuric compounds such as methyl mercaptan (CH₃SH) and dimethyl sulfide (CH₃)₂S, which easily deactivate these metallic sites.

Thus, applying these methods to CST as raw material is not feasible, as Pd catalysts deactivate easily due to coking. For the reactions with CST, more stable catalysts were searched, which besides coking also tolerate the presence of sulfuric compounds. Nonmetallic catalysts, zeolites, proven feasible here, are also applicable to other raw materials comprising α-pinene.

The Method of the Invention

Herein is provided a method, where crude turpentine from wood kraft pulping is desulfurized, dehydrogenated and aromatized in one phase in presence of catalyst. More closely the catalyst is a zeolite catalyzing both isomerization and dehydrogenation consecutively in one reaction step.

Independently from the source of the raw material, herein is provided a method for producing p-cymene, wherein the starting material comprises at least one pinene in gas phase, and a catalyst for conversion comprises zeolite. This provides an alternative for prior art methods, wherein palladium-containing catalysts are applied.

To perform in the gas phase, the reaction temperature should be at least 177° C. For the best performance of the zeolite catalyst, it is applied in the temperature range of 177-400° C., preferably 300-350° C. The inventors have found, that these temperatures provide efficient conversion, but are low enough to avoid cracking With lower amount of catalyst 350° is more favorable, with higher amount 300° C. is sufficient enough. At 300° C. there might be 136-isomers left in the product, whereas at 350° C. the cymene production is higher, but also other aromatics and cyclic compounds are obtained.

Without being bound to a theory, the inventors believe, that to control the overall reaction equilibrium, it is beneficial to remove hydrogen from the reaction and/or dilute its concentration with another, preferably inert gas. Therefore, according to an embodiment, the catalyst is applied in presence of $N_2$ or burnt air. Particular methods include applying the catalyst under $N_2$ pressure of 1-30 bar and/or $N_2$ flush.

Figure 4:
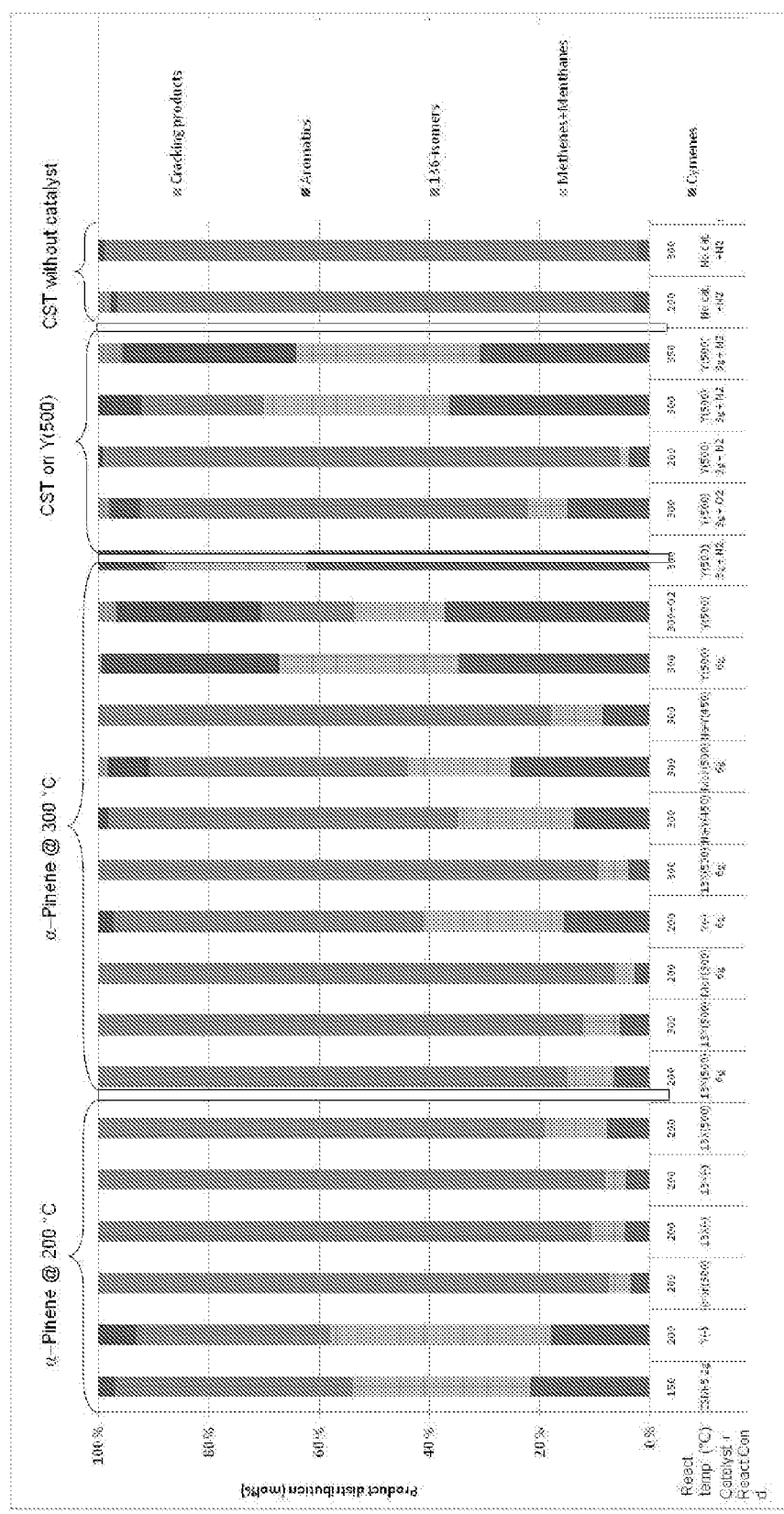
FIG. 4. summarizes the product distribution obtained with the various zeolites at different reaction conditions (T=200-350° C., mcat=0-6 g, α-pinene or CST). On Y faujasite and at 300° C. the yield of cymenes was clearly highest. Product distribution on tested zeolites (13X, Mor, or Y) with varied catalyst amount (0, 3, or 6 g), at reaction temperatures 200-350° C., and with possible addition of $N_2$ or $O_2$ (in air).

The ratio of produced cymenes (M=134 g/mol) to menthenes (M=138 g/mol) and menthanes (M=140 g/mol) is close to unity as can be perceived from FIG. 4. In dehydrogenation to cymenes (Eq. 1), one hydrogen molecule is released versus each cymene molecule formed. The produced hydrogen molecule reacts further hydrogenating a terpene isomer (M=136 g/mol) to menthene (Eq. 2) and/or further to menthane. Theoretically, these two reactions are competing of the same reactant (136-isomer terpene) and, therefore, the fully converted product consists of cymenes and menthenes in ratio 1:1 if hydrogen is not removed from the reaction environment and all hydrogen is supposed to be consumed by hydrogenation (Eq. 2):

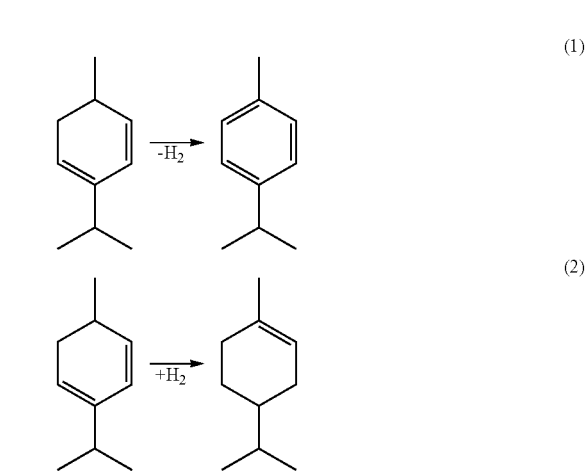

In order to prevent the undesired, competing reaction (hydrogenation) the released hydrogen may removed from the catalyst bed by nitrogen flush thereby increasing the dehydrogenation/hydrogenation ratio.

Figure 5:
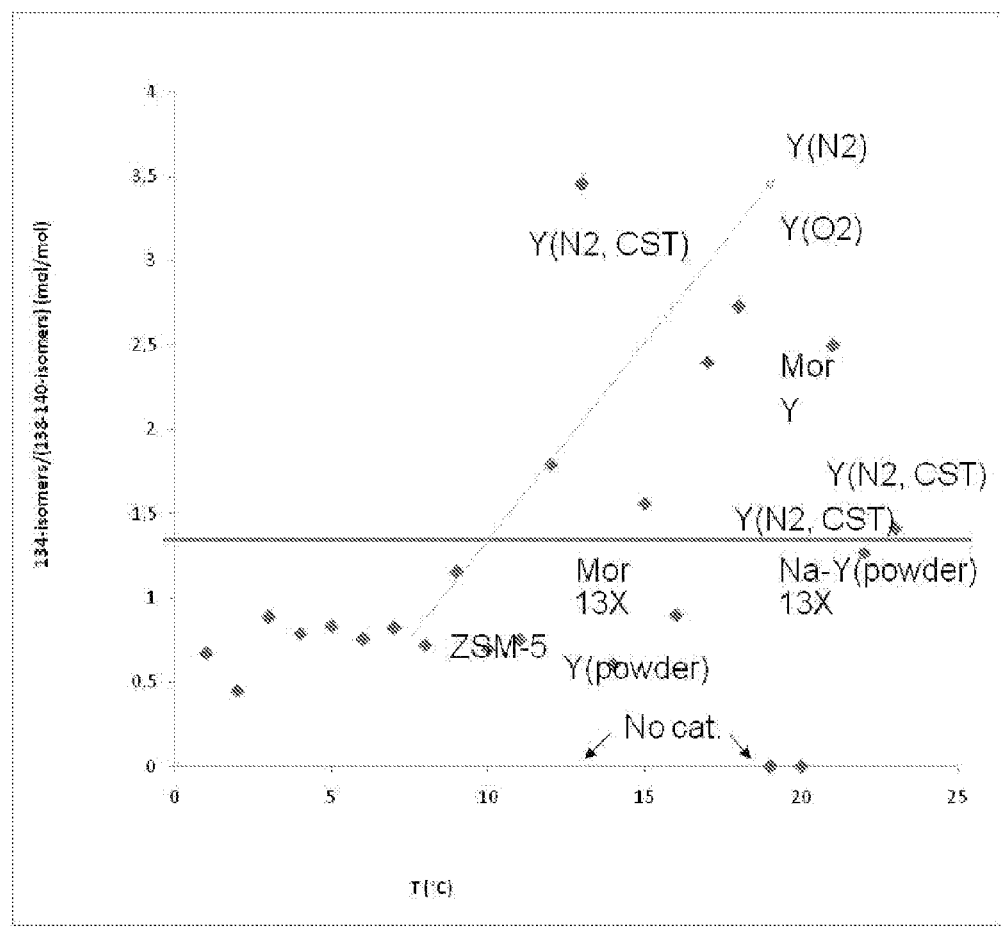
FIG. 5. provides dehydrogenation/hydrogenation ratio as function of reaction temperature on various catalysts with varied reaction conditions and feed (CST or α-pinene).
Figure 6:
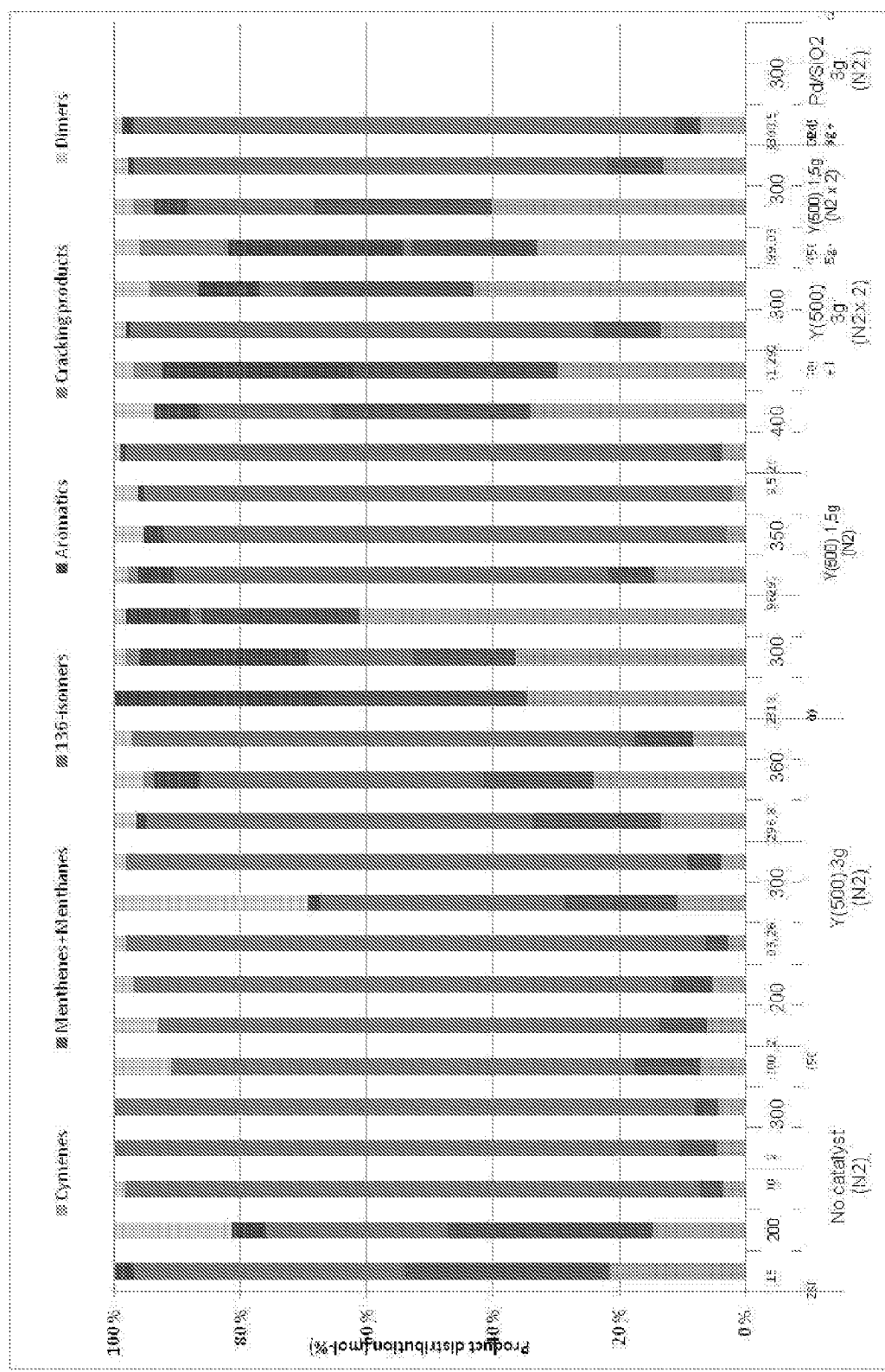
FIG. 6. summarizes the product distribution obtained with the zeolites Y in comparison to Pd-catalyst (or no catalyst), at different reaction conditions (T=200-400° C., mcat=0-3 g, α-pinene or CST). Product distribution on zeolite Y with varied catalyst amount (1.5 or 3 g), at reaction temperatures 200-400° C., and with addition of $N_2$.

As perceived from FIG. 5, the dehydrogenation/hydrogenation ratio was also improved with increased reaction temperature and additional $N_2$ flush. Indeed, the concentration of cymenes was doubled (FIG. 4), when the catalyst bed size and the $N_2$ flow through the catalyst bed were adjusted. When using CST as feed, production of cymene was even further increased (FIG. 6).

The inventors have also found, that the sulfur derivatives, which have been considered as a problem in the conversion reaction, unexpectedly act as $H_2$ acceptors affecting said ratio.

Alternatively, the liberated hydrogen can be reacted with $H_2$ acceptors such as sulfuric compounds that are present in CST, or additional oxygen feed [6], forming $H_2S$ and $H_2O$, respectively. The possible reactions (Eq. 3-5) between the sulfuric compounds and hydrogen are as follows:

$$CH_3SH + H_2 = CH_4 + H_2S \text{ (hydrogenolysis)} \quad (3)$$

$$2CH_3SH = (CH_3)_2S + H_2S \text{ (disproportion)} \quad (4)$$

$$(CH_3)_2S + 2H_2 = 2CH_4 + H_2S \text{ (reduction)} \quad (5)$$

Surprisingly very good results were obtained combining both applying $N_2$ reaction conditions with CST as starting material. Thereby, a high ratio of produced cymenes to menthenes and menthanes was obtained in temperature as low as 200° C.

Biobased p-cymene

In one aspect the invention provides biobased p-cymene obtainable by the process described. This p-cymene can be further refined into biobased terephtalate and eventually for example biobased PET.

Catalyst

In one extension, the method involves zeolites containing alkaline or earth alkaline metals.

Zeolite

In embodiments of the present invention, zeolites were applied as catalysts. Particularly the zeolite is selected from 13X, mordenite (Mor) and Y faujasite, which showed enhanced production of p-cymene from p-pinene. More particularly is Y faujasite zeolite, which provided very high conversion in the method of the invention. Use of Y faujasite zeolite as a catalyst for conversion of α-pinene to p-cymene provided surprisingly good results. Especially, when CST was used as starting material for the conversion reaction, a yield of 80-90% from α-pinene to p-cymene was demonstrated. Further, the conversion of α-pinene was practically 100%, although the product distribution between isomerization and dehydrogenation varied.

According to one embodiment, wherein prior to conversion reaction, the catalyst is pretreated at temperature of 300-500° C. under vacuum. Particularly the pretreatment duration is at least 2 hours.

Suitable catalysts and optimal reaction conditions for p-cymene production from CST and its main compound α-pinene were sought and promising results were obtained at temperatures close to 300° C. with Y faujasite zeolite under 5 bar $N_2$ pressure and additional $N_2$ flush. The high yield of dehydrogenated products can be further improved by adjustment of reaction conditions.

EXAMPLES

The effect obtained was demonstrated experimentally. The reaction was performed in gas phase. Thus, the boiling point of the feed determined the minimum reaction temperature investigated.

Furthermore, due to the presence of sulfur in CST metallic catalysts were excluded from the studies to prevent their poisoning.

The size of the reactor system ($d_i$=10 mm) and the desired weight hourly space velocity (WHSV) of 1.5- about 7 l/h determined the catalyst bed size and the throughput rate. The catalyst loading in examples varied between 1.5 g-6 g. Catalyst particles are extrudates with diameter of 1 mm.

Methods

The conversion of CST and its main compound α-pinene to cymenes was investigated in a continuous tubular flow reactor. The catalyst bed was placed in the middle of the tubular reactor and a temperature measurement element was placed inside the catalyst bed to follow the temperature profile. Before the experiment the catalyst was pre-treated at 300-500° C. for 2 hours under vacuum. The feed was vaporized prior to the reactor. The product flow was cooled down after the reactor and a liquid sample was collected in a cold trap for gas chromatography-mass spectrometry (GC-MS) analysis.

The analysis of the liquid sample was performed with GC-MS. The results were calculated with a method of external standard. p-Cymene and α-pinene were calculated quantitatively. Terpenes and aromatics were calculated semiquantitatively with the responses of α-pinene and p-cymene, respectively. The uncertainty of the measurements was ±15% for p-cymene and α-pinene and ±30% for semiquantitatively calculated compounds. The analysis method was double-checked with two other analysis equipment, GC and GC-MS.

Results

Catalyst

Figure 2:
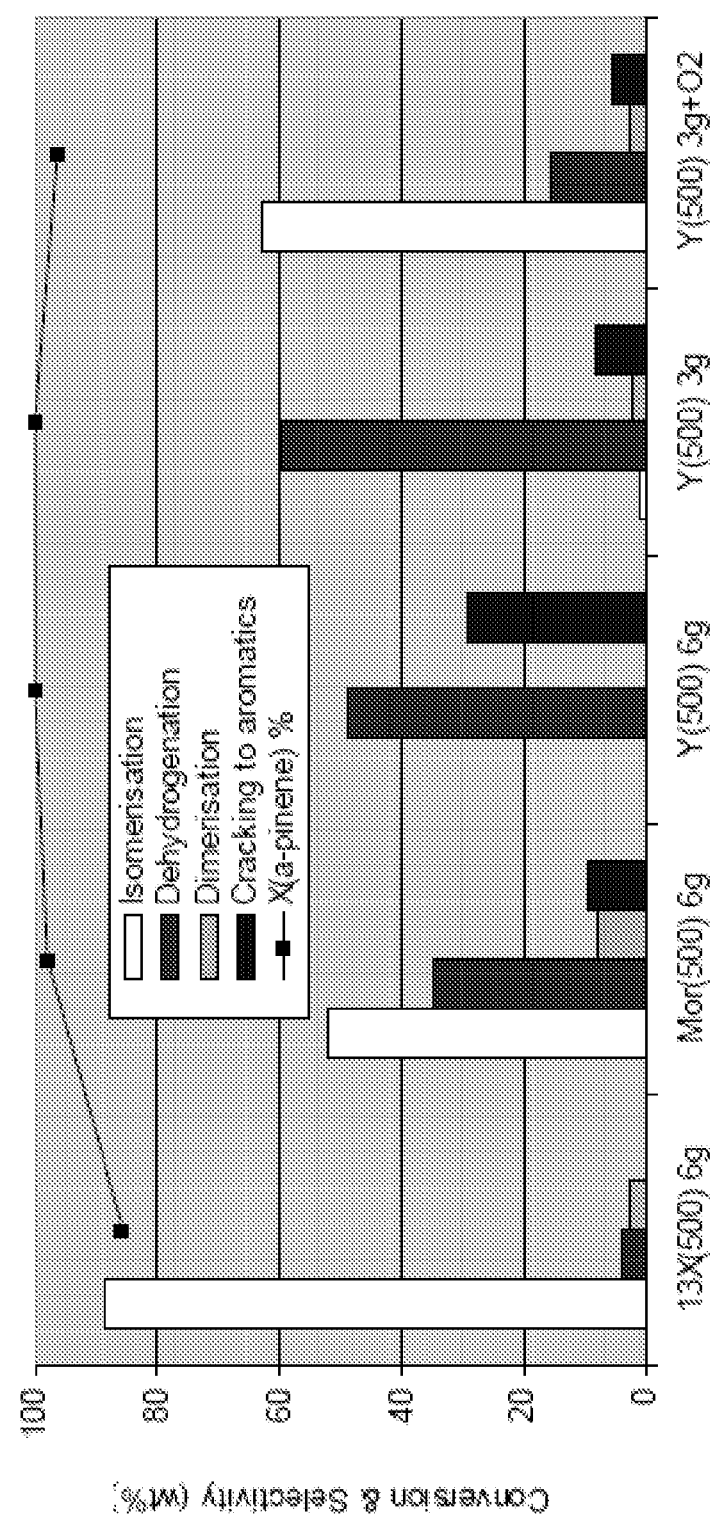
FIG. 2. provides α-pinene conversions and catalyst selectivities to isomerization, dehydrogenation, cracking, and dimerization reactions at 300° C. Y faujasite zeolite showed highest selectivity to dehydrogenation. Results obtained in the presence of $O_2$ (in air) are also shown.

Zeolites (ZSM-5, 13X, mordenite (Mor), Y faujasite (Y)) were compared at a temperature range from 150 to 400° C. in reactions of α-pinene. The experiments were performed in a continuous tubular flow reactor system. At temperatures 150-200° C. the α-pinene conversions (X) were between 50-80% over all other catalyst than Y faujasite (X=100%), and these catalysts were mainly active for isomerization, when the minimum catalyst amount was 3 g. FIG. 2 presents α-pinene conversions and catalyst selectivities to isomerization, dehydrogenation, cracking, and dimerization reactions at 300° C. The selectivity to dehydrogenation was highest on the Y faujasite zeolite. By adjusting other reaction conditions (size of catalyst bed and $N_2$ flush) the selectivity to dehydrogenation products was increased up to 60%. Demonstratively also results obtained in the presence of $O_2$ (in air) are shown in FIG. 2.

Reaction Temperature

Figure 3:
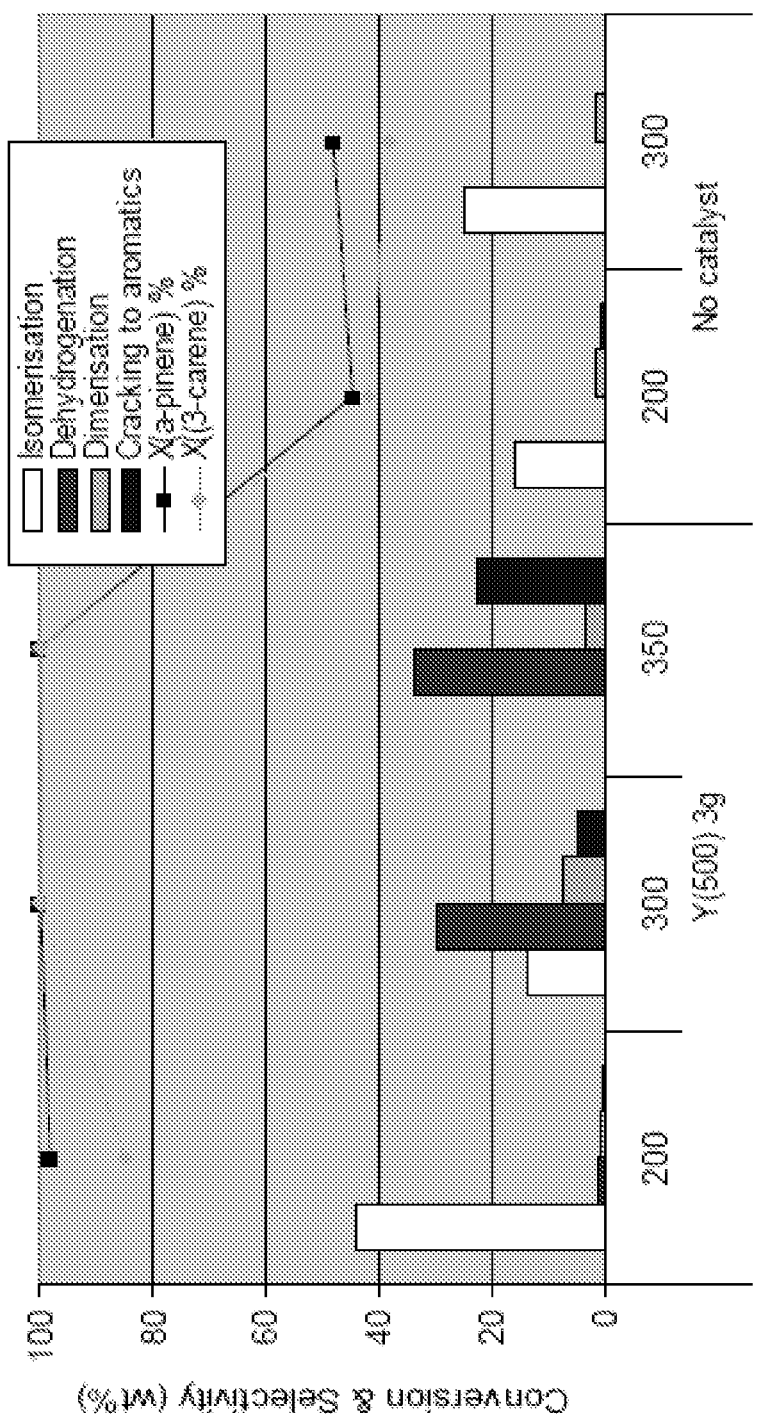
FIG. 3. provides a graph illustrating the conversion (X) and selectivities in experiments with CST at 200-350° C. in the presence and absence of Y faujasite.

The effect of reaction temperature (from 200° C. up to 400° C.) was examined also with CST in the presence and absence of Y-faujasite zeolite (FIG. 3). As from FIG. 3 is observed, it is essential to exploit a catalyst into the reactions from CST to p-cymene.

Without catalyst (i.e. thermal reaction) the conversion levels of α-pinene (M=136 g/mol) and 3-carene (M=136 g/mol) remained below 50% even at high temperature (300° C.) and mainly isomerization reactions proceeded yielding in terpene isomers (M=136 g/mol). In other words, a catalyst seemed to be essential for the second step (dehydrogenation) to proceed, but also to increase the reaction rate of isomerization.

The reaction temperature between 300-350° C. and other parameters had to be adjusted to obtain high yields of cymenes. Indeed, with increased temperature the selectivity to dehydrogenation improved. Also undesired cracking reactions were enhanced with temperature (FIG. 3). However, the amount of undesired cracking products can be controlled with the WHSV through the catalyst bed. By now, even better results obtained at 350° C. with 1.5 g of catalyst.

FIG. 4 summarizes the product distribution obtained with the various zeolites at different reaction conditions (T=200-400° C., mcat=0-6 g, α-pinene or CST). On Y faujasite and at 300° C. the yield of cymenes was very high. With lower catalyst amount, even better results were obtained at 350° C.

The ratio of produced cymenes (M=134 g/mol) to menthenes (M=138 g/mol) and menthanes (M=140 g/mol) is close to unity as can be perceived from FIG. 4. In dehydrogenation to cymenes (Eq. 1), one hydrogen molecule is released versus each cymene molecule formed. The produced hydrogen molecule reacts further hydrogenating a terpene isomer (M=136 g/mol) to menthene and/or further to menthane. Theoretically, these two reactions are competing of the same reactant (136-isomer terpene) and, therefore, the fully converted product consists of cymenes and menthenes in ratio 1:1 if hydrogen is not removed from the reaction environment and all hydrogen is supposed to be consumed by hydrogenation.

In order to prevent the undesired, competing reaction (hydrogenation) the released hydrogen was removed from the catalyst bed by nitrogen flush thereby increasing the dehydrogenation/hydrogenation ratio. The effect of $N_2$ flush and smaller catalyst bed size (or higher WHSV) is compiled in Table 1.

TABLE 1

Molar ratios of conversion products obtained.
Cymenes/Menthaenes molar ratio, CST as feedstock

| mcat (g) | WHSV (1/h) | Reaction temperature (° C.) | | | | |
|---|---|---|---|---|---|---|
| | | 200 | 300 | 350 | 400 | 300 + increased N2 flush |
| 1.5 | 6.67 | n.a. | 1.25 | 1.60 | 1.67 | 1.46 |
| 3 | 3.33 | 2.26 | 1.08 | 0.93 | n.a. | 1.43 |

NOTE:
at 200 C., high amounts of 136-isomers remained, whereas at 350-400 hardly any 136-isomers left.

The dehydrogenation/hydrogenation ratio is presented as the ratio of 134-terpenes to 138/140-terpenes found in the product (FIG. 5).

As perceived from FIG. 5, the dehydrogenation/hydrogenation ratio was also improved with increased reaction temperature and additional $N_2$ flush. Indeed, the concentration of cymenes was doubled (FIG. 4), when the catalyst bed size and the $N_2$ flow through the catalyst bed were adjusted.

Although, the presence of $O_2$ favored the dehydrogenation to hydrogenation ratio, strong deactivation of the Y faujasite was observed only after 6 hours on stream. The deactivation was noticed as decreased conversion level of α-pinene and suppressed dehydrogenation selectivity thereby emphasizing the isomerization reactions (FIG. 2). The deactivation was caused by strong coke deposition of $C_1$-compounds e.g. by Boudouard reaction (Eq. 6). In the presence of sulfur (CST), on the other hand, no deactivation of Y faujasite was observed.

$$2CO = C + CO_2 \text{ (Boudouard)} \qquad (6)$$

With very acidic catalysts or catalyst powders the hydrogenation was stronger than dehydrogenation (ratio of 134-terpenes to 138/140-terpenes <1 in FIG. 5), which was not the objective. Indeed, hydrogen is released in cracking reactions that are enhanced on these acid catalysts thereby promoting hydrogenation. Also, a too long residence time in the catalyst bed (powders) increases the formation of undesired side products such as hydrogenated compounds (FIG. 5), dimerization products, and cracking products.

The invention claimed is:

1. A method for producing a p-cymene, the method comprising:
   providing a sulphurous starting material, comprising at least one pinene in a gas phase and having a sulphur content of at least 0.15 w-%, wherein the sulphurous starting material comprises crude sulphur turpentine (CST);
   contacting said sulphurous starting material with a catalyst comprising Y-faujasite zeolite having a molar ratio of $SiO_2/Al_2O_3$ in a range of 5.2 to 7.5; and
   catalytically converting the at least one pinene in the sulphurous starting material to p-cymene at a reaction temperature in a range of 177° C. to 350° C.

2. The method according to claim 1, wherein the catalyst consists of Y-faujasite zeolite, being free from added transition or noble metal compounds.

3. The method according to claim 1, wherein the at least one pinene comprises α-pinene.

4. The method according to claim 1, wherein the sulphur content of the sulphurous starting material is between at least 0.15 w-% and 1.0 w-%.

5. The method according to claim 4, wherein the sulphurous starting material comprises crude sulfur turpentine (CST) obtained from wood pulping.

6. The method according to claim 1, wherein the reaction temperature is in a range of 300° C. to 350° C.

7. The method according to claim 1, wherein prior to the step of catalytic conversion, the method comprises:
   pretreating the catalyst at a temperature of 300° C. to 500° C. under vacuum.

8. The method according to claim 7, wherein the catalyst is pretreated for at least two hours.

9. The method according to claim 1, wherein the reaction temperature is in the range of 177° C. to 300° C.

10. The method according to claim 1, wherein the sulphurous starting material contacts said catalyst in the presence of $N_2$ or burnt air under a gas pressure of 1 to 30 bar.

11. The method according to claim 1, wherein the sulphurous starting material contacts said catalyst under a $N_2$ flush.

* * * * *